United States Patent
Whitmore, III

(10) Patent No.: US 6,676,623 B2
(45) Date of Patent: Jan. 13, 2004

(54) DRAINAGE DEVICES AND METHODS

(75) Inventor: Willet F. Whitmore, III, Sarasota, FL (US)

(73) Assignee: SciMed Life Systems, Inc., Maple Grove, MN (US)

(*) Notice: Subject to any disclaimer, the term of this patent is extended or adjusted under 35 U.S.C. 154(b) by 82 days.

(21) Appl. No.: 09/849,202

(22) Filed: May 4, 2001

(65) Prior Publication Data

US 2002/0173754 A1 Nov. 21, 2002

(51) Int. Cl.$^7$ .............................................. A61M 5/00

(52) U.S. Cl. ........................ 604/8; 604/264; 604/8; 604/523

(58) Field of Search ........................ 604/8, 264, 9, 604/527, 523, 48, 10; 623/1.15

(56) References Cited

U.S. PATENT DOCUMENTS

| | | |
|---|---|---|
| 191,775 A | 6/1877 | Parsons |
| 3,394,705 A | 7/1968 | Abramson ............... 128/349 |
| 3,485,234 A | 12/1969 | Stevens .................... 128/2 |
| 3,612,050 A | 10/1971 | Sheridan ............... 128/214.4 |
| 3,633,579 A | 1/1972 | Alley et al. ........... 128/214.4 |
| 3,746,003 A | 7/1973 | Blake et al. ........... 128/349 B |
| 3,828,767 A | 8/1974 | Spiroff .................. 128/2.05 |
| 3,902,492 A | 9/1975 | Greenhalgh ............. 128/241 |
| 4,069,814 A | 1/1978 | Clemens ................. 128/2 F |
| 4,129,129 A | 12/1978 | Amrine .................. 128/214 |
| 4,134,402 A | 1/1979 | Mahurkar ............... 128/214 |
| 4,138,457 A | 2/1979 | Rudd et al. ............ 264/500 |
| 4,144,884 A | 3/1979 | Tersteegen et al. ...... 128/214.4 |
| 4,149,535 A | 4/1979 | Volder ................. 128/214.4 |
| 4,180,068 A | 12/1979 | Jacobsen et al. ........ 128/214 R |
| 4,212,304 A | 7/1980 | Finney ................. 128/349 |
| 4,217,895 A | 8/1980 | Sagae et al. .......... 128/214.4 |
| 4,239,042 A | 12/1980 | Asai .................. 128/214.4 |
| 4,307,723 A | 12/1981 | Finney ................ 128/349 |
| 4,327,722 A | 5/1982 | Groshong et al. ....... 128/214.4 |
| 4,403,983 A | 9/1983 | Edelman et al. ........ 604/43 |
| 4,413,989 A | 11/1983 | Schjeldahl et al. ..... 604/96 |
| 4,451,252 A | 5/1984 | Martin ................ 604/43 |
| 4,456,000 A | 6/1984 | Schjeldahl et al. ..... 128/1 D |

(List continued on next page.)

FOREIGN PATENT DOCUMENTS

| | | |
|---|---|---|
| DE | 3517813 A1 | 11/1986 |
| DE | 37 40 288 C1 | 4/1989 |

(List continued on next page.)

OTHER PUBLICATIONS

Mardis et al., "Comparative Evaluation of Materials Used for Internal Ureteral Stents," *Journal of Endourology*, 1993, vol. 7, No. 2, (pp. 105–113).

Collier et al., "Proximal Stent Displacement As Complication of Pigtail Ureteral Stent," *Urology*, Apr. 1979, vol. XIII, No. 4, (pp. 372–375).

(List continued on next page.)

*Primary Examiner*—Ira S. Lazarus
*Assistant Examiner*—Camtu Nguyen
(74) *Attorney, Agent, or Firm*—Testa, Hurwitz & Thibeault, LLP

(57) ABSTRACT

A ureteral drainage stent is designed to be placed in a patient's ureter and extend into a patient's bladder. An elongated tubular segment includes a distal region for placement in the renal cavity, and a proximal region for placement in a urinary bladder. A central lumen connects at least one opening in the distal region to at least one opening in the proximal region. The elongated segment is constructed such that the wall surrounding the lumen is thinner in the proximal region than in the distal region. The thin-walled portion of the elongated segment extends along at least part of the ureter, across the ureteral vesicle junction, and from there into the bladder.

45 Claims, 8 Drawing Sheets

U.S. PATENT DOCUMENTS

| | | | |
|---|---|---|---|
| 4,531,933 A | 7/1985 | Norton et al. ................... 604/8 |
| 4,543,087 A | 9/1985 | Sommercorn et al. ......... 604/43 |
| 4,559,046 A | 12/1985 | Groshong et al. ........... 604/282 |
| 4,581,012 A | 4/1986 | Brown et al. .................. 604/43 |
| 4,583,968 A | 4/1986 | Mahurkar ..................... 604/43 |
| 4,596,548 A | 6/1986 | DeVries et al. ................. 604/4 |
| 4,610,657 A | 9/1986 | Densow .......................... 604/8 |
| 4,619,643 A | 10/1986 | Bai ............................... 604/43 |
| 4,643,716 A | 2/1987 | Drach ............................ 604/8 |
| 4,671,795 A | 6/1987 | Mulchin ..................... 604/281 |
| 4,682,978 A | 7/1987 | Martin .......................... 604/43 |
| 4,692,141 A | 9/1987 | Mahurkar ..................... 604/43 |
| 4,713,049 A | 12/1987 | Carter ............................ 604/8 |
| 4,738,667 A | 4/1988 | Galloway ................... 604/281 |
| 4,769,005 A | 9/1988 | Ginsburg et al. ............. 604/53 |
| 4,770,652 A | 9/1988 | Mahurkar ....................... 604/4 |
| 4,787,884 A | 11/1988 | Goldberg ....................... 604/8 |
| 4,790,809 A | 12/1988 | Kuntz ............................ 604/8 |
| 4,790,810 A | 12/1988 | Pugh, Jr. et al. ................ 604/8 |
| 4,813,429 A | 3/1989 | Eshel et al. .................. 128/736 |
| 4,813,925 A | 3/1989 | Anderson, Jr. et al. ......... 604/8 |
| 4,820,262 A * | 4/1989 | Finney ........................... 604/8 |
| 4,842,590 A | 6/1989 | Tanabe et al. .............. 604/282 |
| 4,863,424 A * | 9/1989 | Blake, III et al. ............ 604/54 |
| 4,863,442 A | 9/1989 | DeMello et al. ............ 604/282 |
| 4,865,595 A * | 9/1989 | Heyden ....................... 604/352 |
| 4,874,360 A * | 10/1989 | Goldberg et al. .............. 604/8 |
| 4,913,683 A * | 4/1990 | Gregory ......................... 604/8 |
| 4,931,037 A | 6/1990 | Wetterman ..................... 604/8 |
| 4,950,228 A | 8/1990 | Knapp, Jr. et al. .............. 604/8 |
| 4,961,809 A | 10/1990 | Martin ....................... 156/294 |
| 4,981,482 A | 1/1991 | Ichikawa .................... 606/108 |
| 4,983,169 A | 1/1991 | Furukawa ................... 604/164 |
| 4,990,133 A | 2/1991 | Solazzo ......................... 604/8 |
| 4,995,865 A | 2/1991 | Gahara et al. ................ 604/43 |
| 4,995,868 A | 2/1991 | Brazier ....................... 604/105 |
| 5,019,102 A | 5/1991 | Hoene .......................... 623/12 |
| 5,041,083 A | 8/1991 | Tsuchida et al. ............. 604/43 |
| 5,045,072 A | 9/1991 | Castillo et al. ............. 604/280 |
| 5,053,004 A | 10/1991 | Markel et al. ................ 604/43 |
| 5,057,073 A | 10/1991 | Martin .......................... 604/43 |
| 5,069,673 A | 12/1991 | Shwab ....................... 604/280 |
| 5,135,599 A | 8/1992 | Martin et al. ............... 156/294 |
| 5,141,502 A * | 8/1992 | Macaluso, Jr. .............. 604/281 |
| 5,167,623 A | 12/1992 | Cianci et al. ................. 604/43 |
| 5,176,625 A | 1/1993 | Brisson .......................... 604/8 |
| 5,176,626 A | 1/1993 | Soehendra ..................... 604/8 |
| 5,188,593 A | 2/1993 | Martin .......................... 604/43 |
| 5,205,830 A | 4/1993 | Dassa et al. ................ 604/164 |
| 5,211,627 A | 5/1993 | William ....................... 604/82 |
| 5,221,253 A | 6/1993 | Coll ............................... 604/8 |
| 5,250,034 A | 10/1993 | Appling et al. ............. 604/164 |
| 5,250,038 A | 10/1993 | Melker et al. .............. 604/264 |
| 5,275,597 A | 1/1994 | Higgins et al. ............... 606/33 |
| 5,282,784 A | 2/1994 | Willard ......................... 604/8 |
| 5,295,954 A | 3/1994 | Sachse .......................... 604/8 |
| 5,318,532 A | 6/1994 | Frassica ...................... 604/96 |
| 5,344,412 A * | 9/1994 | Wendell et al. ............. 604/280 |
| 5,346,467 A | 9/1994 | Coll ............................... 604/8 |
| 5,348,536 A | 9/1994 | Young et al. ................. 604/43 |
| 5,354,263 A | 10/1994 | Coll ............................... 604/8 |
| 5,364,340 A * | 11/1994 | Coll ............................... 604/8 |
| 5,372,600 A | 12/1994 | Beyar et al. ................ 606/108 |
| 5,374,245 A | 12/1994 | Marhurkar ................... 604/43 |
| 5,378,230 A | 1/1995 | Marhurkar ................... 604/43 |
| 5,380,270 A | 1/1995 | Ahmadzadeh ................ 604/9 |
| 5,401,257 A | 3/1995 | Chevalier, Jr. et al. ..... 604/265 |
| 5,405,329 A | 4/1995 | Durand ...................... 604/164 |
| 5,464,398 A | 11/1995 | Haindl ....................... 604/280 |
| 5,470,322 A | 11/1995 | Horzewski et al. ......... 604/280 |
| 5,472,417 A | 12/1995 | Martin et al. ................. 604/43 |
| 5,480,380 A | 1/1996 | Martin .......................... 604/43 |
| 5,531,741 A | 7/1996 | Barbacci ...................... 606/15 |
| 5,599,291 A | 2/1997 | Balbierz et al. ................ 604/8 |
| 5,599,306 A * | 2/1997 | Klein et al. ................... 604/96 |
| 5,647,843 A | 7/1997 | Mesrobian et al. ............ 604/8 |
| 5,647,858 A * | 7/1997 | Davidson .................... 604/264 |
| 5,649,909 A | 7/1997 | Cornelius .................... 604/96 |
| 5,681,274 A | 10/1997 | Perkins et al. ................. 604/8 |
| 5,769,868 A | 6/1998 | Yock .......................... 604/194 |
| 5,868,718 A | 2/1999 | Pepin et al. ................. 604/264 |
| 6,306,105 B1 * | 10/2001 | Rooney et al. ............. 600/585 |
| 6,395,021 B1 * | 5/2002 | Hart et al. .................. 623/1.15 |
| 6,450,987 B1 * | 9/2002 | Kramer ....................... 604/43 |

FOREIGN PATENT DOCUMENTS

| | | |
|---|---|---|
| DE | 41 03 573 A1 | 8/1992 |
| DE | 41 34 030 A1 | 4/1993 |
| DE | 93 14 585.3 | 1/1994 |
| EP | 326 908 A2 | 8/1989 |
| EP | 0333308 A2 | 9/1989 |
| EP | 0386408 A1 | 9/1990 |
| EP | 0554722 A1 | 8/1993 |
| EP | 0 806 189 A1 | 5/1997 |
| FR | 1285953 | 1/1962 |
| FR | 1508959 | 12/1967 |
| FR | 2611486 | 9/1988 |
| WO | WO 97/10858 | 3/1997 |
| WO | WO 97/17094 | 5/1997 |
| WO | WO/97/17094 | * 5/1997 ............ A61M/5/00 |
| WO | WO 97/37699 | 10/1997 |

OTHER PUBLICATIONS

Birch et al., "Tethered Ureteric Stents—a Clinical Assessment," *British Journal of Urology*, 1988, 62, (pp. 409–411).

Mardis et al., "Guidewires, Ureteral Catheters, and Stents," *Color Atlas/Text of Ureteroscopy*, New York, Igaku–Shoin, Ch. 5, (pp. 65–84).

Cook Urological product brochure, "Ureteral Stents," 1987, (pp. 3–23; last page).

Mardis et al., "Ureteral Stents–Materials," *Urologic Clinics of North America*, Aug. 1988, vol. 15, No. 3, (pp. 471–479).

Mardis et al., "Ureteral Stents Use and Complications," *Problems in Urology*, Jun. 1992 vol. 6, No. 2, (pp. 296–306).

Hackethorn et al., "Antegrade Internal Ureteral Stenting: A Technical Refinement," *Radiology*, Jul. 1985, vol. 156, No. 3, (pp. 287–288).

Rutner et al., "Percutaneous Pigtail Nephrostomy," *Urology*, Oct. 1979, vol. XIV, No. 4, (pp. 337–340).

Mardis, "Evaluation of Polymeric Materials for Endourologic Devices," *Seminars in International Radiology*, Mar. 1987, vol. 4, No. 1, (pp. 36–45).

Mardis et al., "Double Pigtail Ureteral Stent," *Urology*, Jul. 1979, vol. XIV, No. 1, (pp. 23–26).

Hepperlen et al., "Self–Retained Internal Ureteral Stents: A New Approach," *The Journal of Urology*, Jun. 1978, vol. 119, (pp. 731–734).

Culkin, "Complications of Ureteral Stents," *Infections in Urology*, Sep./Oct. 1996, (pp. 139–143).

Sadlowski et al., "New Technique For Percutaneous Nephrostomy Under Ultrasound Guidance," *Journal of Urology*, May 1979, vol. 121, (pp. 559–561).

Camacho et al. "Double–Ended Pigtail Ureteral Stent: Useful Modification to Single End Ureteral Stent," *Urology*, May 1979, vol. XIII, No. 5, (pp. 516–520).

Bigongiari et al., "Conversion of Percutaneous Ureteral Stent To Indwelling Pigtail Stent Over Guidewire," *Urology*, May 1980, vol. XV, No. 5, (pp. 461–465).

Minkov et al., "Our Experience in the Application of the Biocompatible Indwelling Ureteral Stents," *International Urology and Nephrology*, 1986, 18 (4), (pp. 403–409).

Mardis et al., "Polyethylene Double–Pigtail Ureteral Stents," *Urologic Clinics of North America*, Feb. 1982, vol. 9, No. 1, (pp. 95–101).

Stables, "Percutaneous Nephrostomy: Techniques, Indications, and Results," *Urologic Clinics of North America*, Feb. 1982, vol. 9, No. 1, (pp. 15–29).

Bard Urological Division product catalog, 1990, (pp. 1–3, A1–A30, D7–D26; last page).

Cook Urological product brochure, "Filiform Ureteral Multi–Length Silicone Stent Sets," 1989.

Bard brochure, "Introducing The Bard Urinary Diversion Stent," 1984.

International Search Report for International Patent Application No. PCT/US02/13918, dated Oct. 9, 2002, 5 pages.

* cited by examiner

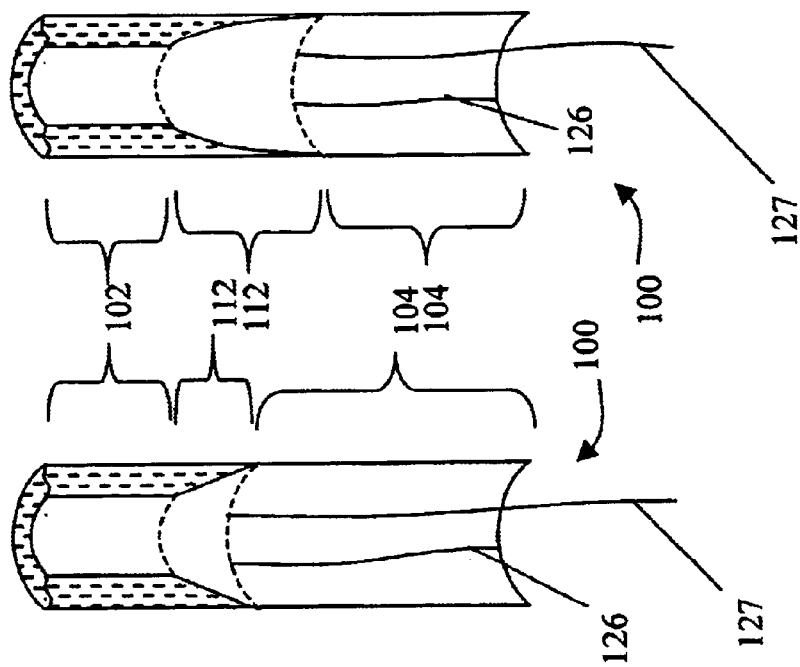
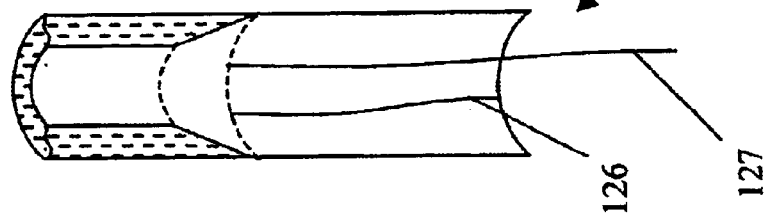
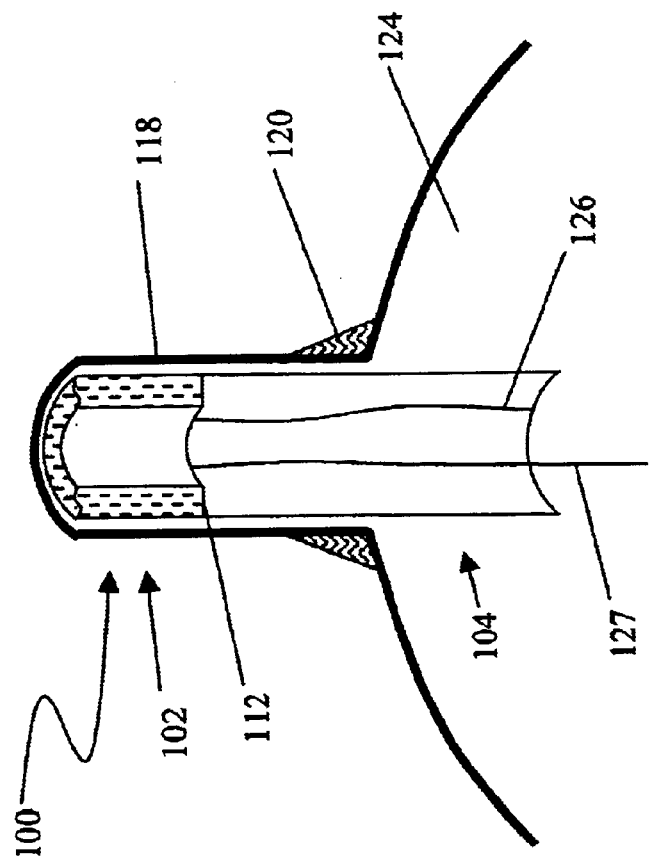

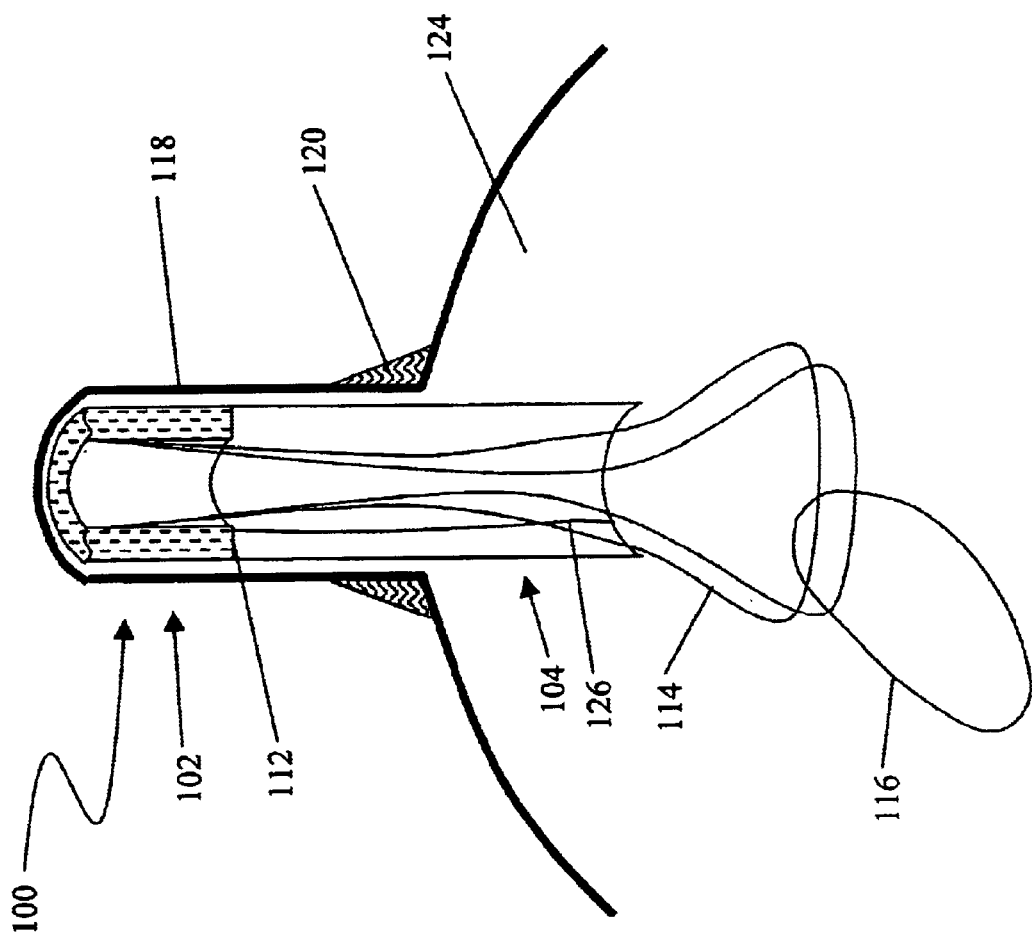

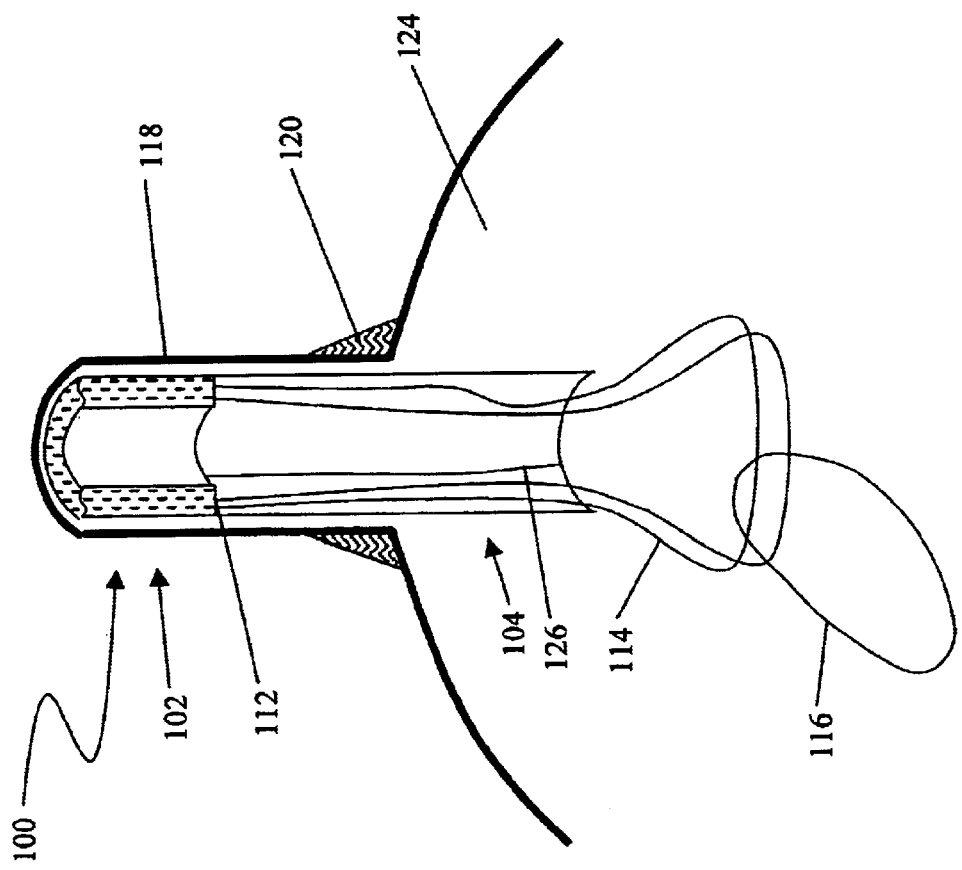

FIG. 7A
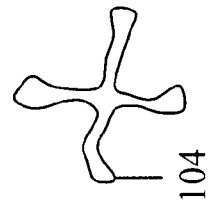
FIG. 7B
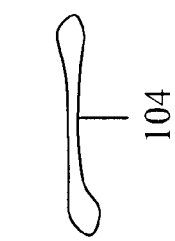
FIG. 7C
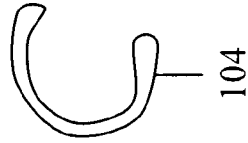
FIG. 7D
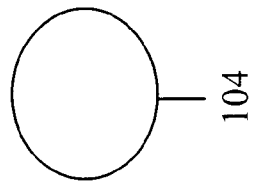
FIG. 7E
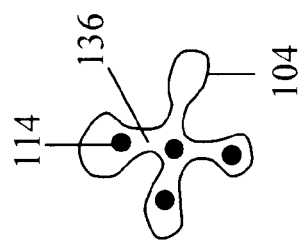
FIG. 7F
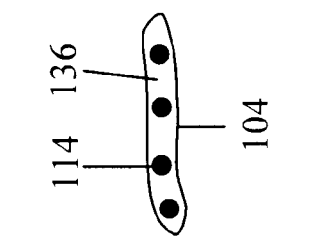
FIG. 7G
FIG. 7H
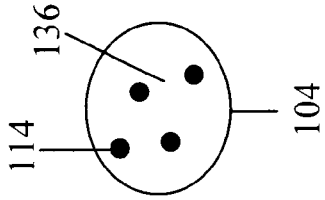

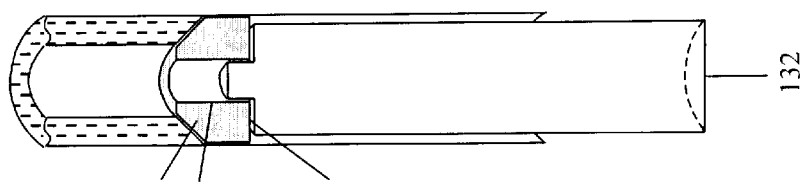
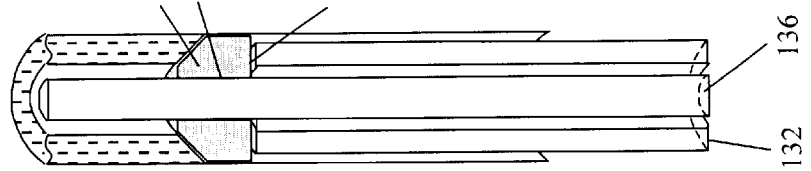
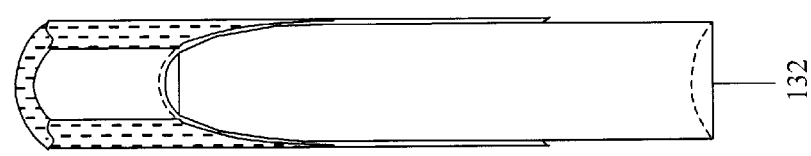
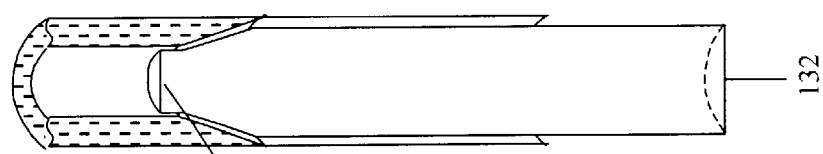
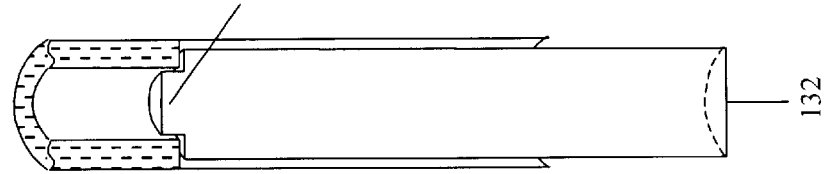
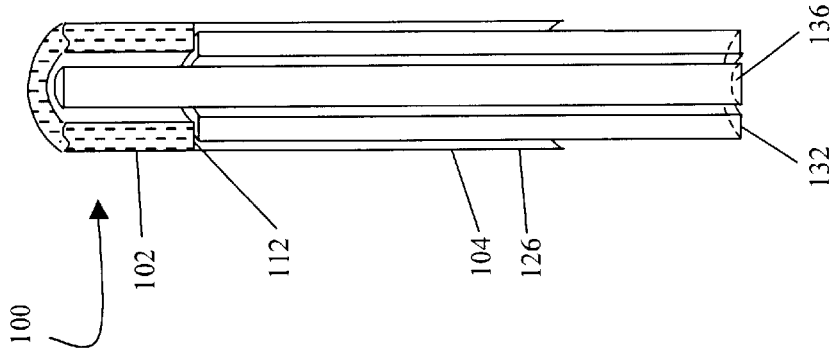

DRAINAGE DEVICES AND METHODS

TECHNICAL FIELD

This invention generally relates to medical devices for drainage of fluids, and more specifically to ureteral stents.

BACKGROUND INFORMATION

Ureteral stents are used to assist urinary drainage from the kidney to the bladder in patients with ureteral obstruction or injury, or to protect the integrity of the ureter in a variety of surgical manipulations. Stents may be used to treat or avoid ureter obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter.

Ureteral stents typically are tubular in shape, terminating in two opposing ends: a kidney distal end and a bladder proximal end. One or both of the ends may be coiled in a pigtail or J-shape to prevent the upward and/or downward migration of the stent due, for example, to physiological movements. A kidney end coil is designed to retain the stent within the renal pelvis and to prevent stent migration down the ureter. The bladder end coil sits in the bladder and is designed to prevent stent migration upward toward the kidney. The bladder coil is also used to aid in retrieval and removal of the stent.

SUMMARY OF THE INVENTION

Ureteral stents, particularly the portion positioned in the ureter near the bladder and inside the bladder, may produce adverse effects including blood in the urine, a continual urge to urinate, strangury, and flank pain accompanying reflux of urine up the stent (e.g., when voiding) as pressure within the bladder is transmitted to the kidney. In short, stents may cause or contribute to significant patient discomfort and serious medical problems.

The present invention concerns a ureteral stent that avoids patient discomfort and urine reflux upward toward the kidney. Patient discomfort induced by the use of a foreign body may be decreased with devices that are as small and flexible as possible in the lower (bladder) end of the ureter and in the bladder itself. Rather than rely on a tubular structure of a substantial set thickness for the entire length of the ureteral stent, the invention concerns a stent with a thin flexible wall at the proximal region of the stent. When the stent is placed within the urinary system of a patient, the proximal region of the stent generally is located in or near the end of the ureter at the junction of the ureter and the urinary bladder and also in the bladder itself, and the distal region generally is located in the kidney and in or near the other end of the ureter at the junction of the ureter and the kidney. In general, the thin-walled proximal region of the stent is sized and configured to extend along at least part of the ureter near the bladder, and may cross the ureteral vesicle junction, and into the bladder. The ureteral vesicle junction is a particularly sensitive region of the ureter and is the source of much of the discomfort resulting from the presence of an installed stent. It also is possible, and in some cases desirable, to use a stent with a thin wall throughout substantially all of its length, from near the kidney retention structure to the proximal region.

The stent wall of the middle and distal regions may be constructed of a material of greater thickness than the proximal region in order to resist the pressure from the adjacent tissue that would collapse the ureter if not for the presence of the stent. The middle region is the elongated region of the stent between the distal region and a transition zone found near the proximal region. Towards the proximal region of the stent, the inner diameter of the wall that exists in the middle and distal regions increases, resulting in a comparatively thinner wall in the proximal region of the stent, while the outer diameter of the stent is constant or substantially constant over the entire length of the stent. The thin wall region can be positioned at or near the ureteral vesicle junction. The thin wall construction at the proximal region of the stent produces a softer and more flexible segment of the stent which decreases the irritation to the surrounding tissues while allowing for normal urine drainage and resistance to urine reflux.

In one aspect, the invention relates to a medical device for assisting the drainage of fluid from a body cavity. The medical device includes an elongated segment extending from a distal region through a transition zone to a proximal region, the segment having a substantially constant outer diameter and an inner wall. The inner wall defines a lumen having an inner diameter in the proximal region that is greater than the inner diameter in the distal region. The transition zone may extend through a middle segment of the stent or all the way from a middle segment to the proximal end. The variation of the inner diameter in the transition zone may be linear or non-linear, steep or smooth, continuous or combinations thereof. The variation of the inner diameter may be quantic resulting in a step change. In one embodiment, the medical device is a stent. In another embodiment the medical device is a ureteral stent.

In some embodiments, the transition zone has no longitudinal length thus forming a step in the inner diameter between the proximal and distal regions. The step forms a surface for contacting a pusher during implantation of the medical device in the body cavity. In other embodiments, the segment includes a pliable proximal region.

In yet other embodiments the medical device further includes at least one member extending through at least some of the lumen to the proximal region. The member may include a flexible material. The member may include a thread. In other embodiments the member is secured to an inner wall. The member may also include a substantially noncompressible material. In some embodiments, the member includes a loop.

In yet another embodiment, the elongated segment includes a retention structure in the distal region. The retention structure may be kink resistant. The retention structure may include a coil.

The device may further include a second segment including an exterior wall contacting at least a portion of the inner wall of the elongated segment, and further including an inner wall defining a lumen coaxial with the lumen of the elongated segment. The second segment may include a surface disposed at a proximal region for contacting a pusher during implantation of the medical device in the body cavity. In one embodiment, the exterior wall of the second tubular segment provides an interference fit with the inner wall of the first segment. In another embodiment, the transition zone includes varying inner diameters of the inner wall between the distal region and the proximal region.

In another embodiment, the medical device includes at least one member extending from the second segment. In yet another embodiment, the member is secured to the elongated segment. In another embodiment, the member includes a flexible material. The member may also include a substantially noncompressible material. The member may include a thread. In some embodiments, the member includes a loop.

In still another aspect, the invention relates to a medical device for assisting the drainage of fluid from a body cavity, the device including an elongated segment having an annular wall defining a lumen, the lumen extending from a distal opening to a proximal opening. The annular wall having a thickness near the distal opening greater than near the proximal opening, wherein the elongated segment is kink resistant near the distal opening and pliable near the proximal opening.

In one embodiment, the medical device includes a stent. The medical device may also include a ureteral stent. In another embodiment, the medical device includes at least one member extending from and attached to the elongated segment. In yet another embodiment, the member includes a thread. In yet another embodiment, the medical device may further include a second segment including an exterior wall contacting at least a portion of the inner wall of the elongated segment, and further including an inner wall defining a lumen coaxial with the lumen of the elongated segment.

In another aspect, the invention relates to a method for treatment of blockage of urine flow from a kidney to a urinary bladder. The method includes providing a medical device and inserting the device in a ureter for assisting the drainage of fluid from a body cavity. The medical device includes an elongated segment extending from a distal region through a transition zone to a proximal region, the segment having a constant outer diameter and an inner wall defining a lumen having an inner diameter in the proximal region that is greater than the inner diameter in the distal region. In an embodiment, the method further includes positioning the distal region of the medical device near a renal pelvis and positioning the proximal region of the medical device in a urinary bladder. In an embodiment, the method includes positioning the transition zone of the stent at least partly upstream of the ureteral junction.

In another embodiment, the method further includes a second segment including an exterior wall contacting at least a portion of the inner wall of the elongated segment, and further comprising an inner wall defining a lumen coaxial with the lumen of the elongated segment.

In another aspect, the invention relates to a method for treatment of blockage of urine flow from a kidney to a urinary bladder. The method includes providing a medical device and inserting the device in a ureter for assisting the drainage of fluid from a body cavity. The medical device includes an elongated segment having an annular wall defining a lumen, the lumen extending from a distal opening to a proximal opening. The annular wall includes a thickness near the distal opening greater than near the proximal opening, wherein the elongated segment is kink resistant near the distal opening and pliable near the proximal opening. In an embodiment, the method further includes positioning the distal region of the medical device near a renal pelvis and positioning the proximal region of the medical device in a urinary bladder. In an embodiment, the method includes positioning the transition zone of the stent at least partly upstream of the ureteral junction.

The positioning of a stent may include the use of a pusher. In one embodiment, the distal end of the pusher contacts a surface of the stent in the transition zone. In another embodiment, the distal end of the pusher is tapered and directly abuts the stent in the transition zone. In yet another embodiment, the pusher contacts a surface on a second segment disposed within the lumen of the stent near the transition zone.

The foregoing and other aspects, embodiments, features, and advantages of the invention will become apparent from the following description, figures, and claims.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention.

FIGS. 2A–C depict various embodiments of the proximal region of the medical device of FIG. 1 in longitudinal cross-section, with FIG. 2A showing the proximal region positioned in the ureter and urinary bladder, and FIGS. 2B and 2C showing this region outside of the body of a patient.

FIG. 5 depicts still another embodiment of a proximal region of a medical device of the invention in longitudinal cross-section positioned in the ureter and urinary bladder.

FIG. 6 depicts yet still another embodiment of a proximal region of a medical device of the invention in longitudinal cross-section positioned in the ureter and urinary bladder.

FIGS. 7A–D depict four examples of a transverse cross-sectional view of the proximal region of a medical device of the invention, without tail members.

FIGS. 7E–H depict four examples of a transverse cross-sectional view of the proximal region of a medical device of the invention, with tail members.

FIGS. 8A–F depict various embodiments of a distal end of a pusher, each contacting a landing within a transition zone of a stent according to the invention, as occurs during installation of the stent.

DESCRIPTION

Figure 1B:
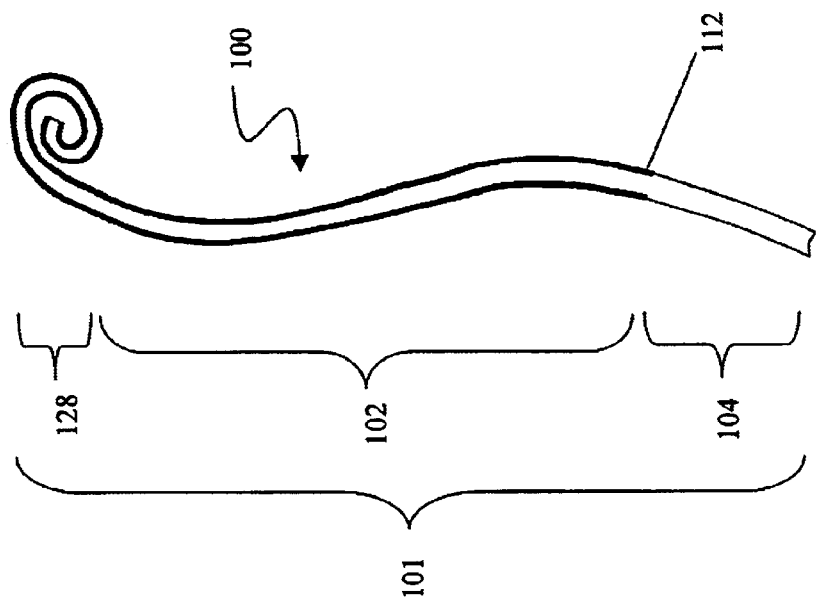
FIGS. 1A–B depict an embodiment of a medical device of the invention, with FIG. 1A showing the device positioned in a ureter with a distal region in a kidney and a proximal region in a ureteral vesical junction and bladder, and FIG. 1B showing the device outside of the body.

This invention generally concerns a drainage device that, when positioned within a body cavity of a mammal, significantly reduces discomfort to the patient such as a ureteral stent positioned in the ureter of a human. A ureteral stent assists in the flow of urine from the kidneys to the urinary bladder. The structure of the proximal region of the stent according to this invention provides an increase in comfort for the patient. The region known as the ureteral vesical junction is a small area of the ureter that is located immediately prior to the ureter joining the urinary bladder. The ureteral vesical junction has substantially greater sensitivity relative to other regions of the ureter wall and kidneys and is a major source of patient discomfort when in contact with indwelling ureteral stents.

The wall thickness at the proximal region of a stent of the invention is reduced for the purpose of making the region more pliable, flexible, and supple to adapt or partially yield to the closing or narrowing of the ureter in the junction during constriction. A pliable wall is such that an annular wall of a stent will collapse, bend, and fold upon itself upon pressure exerted by body tissue within a cavity, peristaltic motion or sphincter contraction, for example. A suitable pliable wall may be constructed from biocompatible plastics or polymers including PTFE, silicone polyurethane, polyurethane plastics, polyethylene plastics, and thermoplastics and have a wall thickness of 0.5/1000 to 15/1000 inch, for example. A pliable, flexible, and supple proximal region will chafe and irritate the ureteral vesical junction to a lesser degree thus increasing the comfort level of the patient. The thin-walled proximal region of the stent facilitates normal drainage of urine through the stent while maintaining resistance to urine reflux upward toward the kidney. Typically, the thin-walled construction of the stent is sized and configured with a length sufficient to extend at least along the ureteral vesical junction and into the urinary bladder. However, the thin-walled construction may also be sized and configured with a length sufficient to extend the whole length of the ureter. A suitable length of the thin wall may be selected as small as 0.5 inch and as long as 10 inches.

The stent wall in the distal region is sufficiently thick to be kink-resistant and maintain patency of the vessel despite constriction or removing of the vessel due to enlargement of tissue surrounding it or peristaltic motions. A kink resistant wall is such that the annular wall of the stent does not collapse upon itself upon radial or lateral pressure of the surrounding body tissue when positioned to drain a body cavity of a mammal or upon longitudinal pressure exerted during insertion of the stent into the body cavity. Kink resistant properties may be imparted to a stent by varying the thickness of the wall of the stent depending on the softness or sturdiness of the material used to manufacture the stent—for example, a wall thickness of $1/32$ to $1/16$ inch may be used with materials such as silicone, PTFE, polyurethane plastics, and polyethylene plastics.

The stent of this invention may include an elongated segment that has an annular wall with a substantially constant outer diameter and an inner diameter that defines a lumen extending from a distal region, through a middle region and transition zone to a proximal region. The lumen has a proximal inner diameter greater than a distal inner diameter, and varying inner diameters in the transition zone that transition from the proximal inner diameter to the distal inner diameter. The wall near the distal region is kink resistant and the wall near the proximal region is pliable. The cross-sectional geometry of the stent may be any shape that allows the flow of liquid through the segment including round, oblong, elliptical, hexagonal, D-shaped, crescent-shaped, square, for example. The stent may be constructed from biocompatible plastics or polymers including PTFE, silicone polyurethane, polyurethane plastics, polyethylene plastics, and thermoplastics, for example. Construction of the stent may be performed by injection or extrusion molding, for example.

The stent of the invention may further include one or more members, elongated thread-like structures attached at one or both ends to the stent. The members may include threads, fibers, tubes, strings, for example. Members may be of varied lengths and thickness. Members may have a thickness between 0.2 and 1.0 mm, for example. Members may be constructed from a variety of materials including, biocompatible plastic, natural fibers, glass fibers, or rubber, for example. Members assist in drainage by functioning as a fluid transport surface and by creating interstitial spaces between members and between members and the inner wall of the stent for urine to flow through. Members may be incorporated into the stent during the molding process or extrusion process. Alternatively, the member may be incorporated into the stent after the first or second segments have been constructed. Members may also be embedded in the wall of the proximal region during the molding process or extrusion process. Members embedded in the wall of the proximal region have sufficient tensile strength to allow their use as a handle to remove the stent from the body.

The stent may further include an extraction thread that may be embedded in the wall of the proximal region. The extraction thread serves to reinforce and increase the resistance to tearing of the thin wall in the region. The extraction thread may or may not extend beyond the proximal end of the stent. An extraction thread that does not extend beyond the proximal end of the stent serves to strengthen the thin wall of the stent at the proximal region. An extraction thread that does extend beyond the proximal end of the stent further functions as a graspable structure of the stent for removal of the stent from the ureter.

Figure 1A:
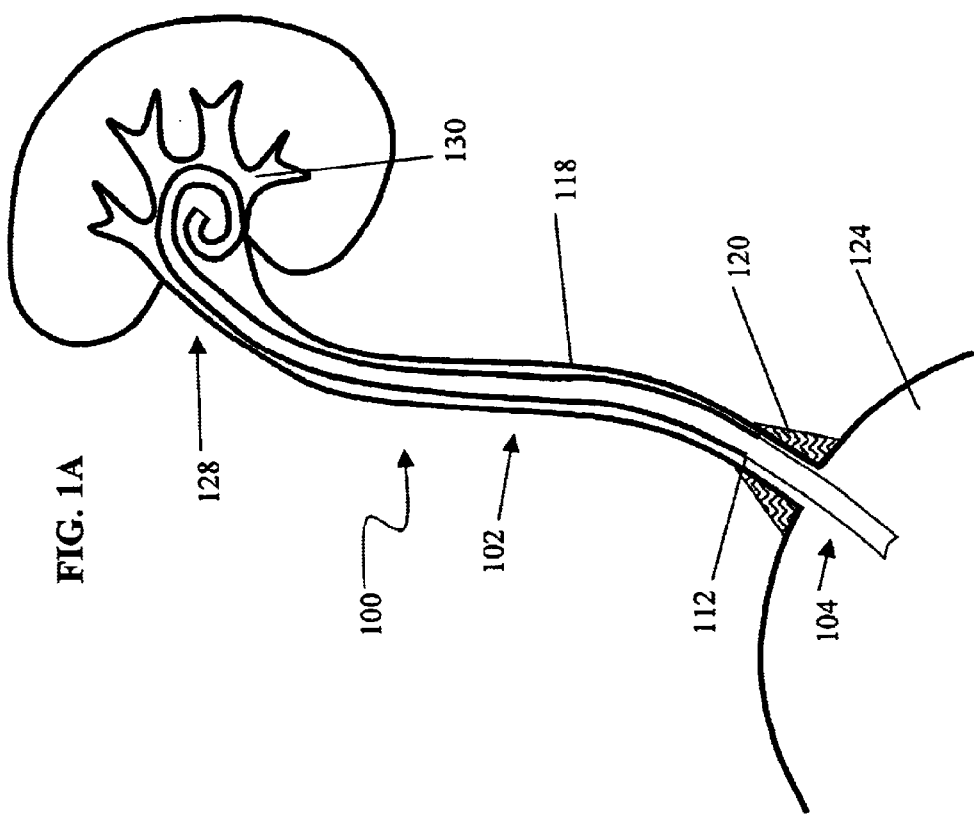

In FIG. 1A, a ureteral stent 100 includes an elongated segment 101 that has a constant or at least a substantially constant outer diameter, and that has an inner diameter that defines a lumen extending from a distal region 128 through a middle region 102 and transition zone 112 to a proximal region 104. The kink resistant distal region 128 forms a coil or other retention structure or shape that functions as an anchor to retain the stent within the renal pelvis and calyx 130 of the kidney and to prevent migration of the stent up or down the ureter 118. Alternatively, other geometry may be suitably used as anchors. The stent wall in the proximal region 104 of stent 100 is substantially thinner than the stent wall of the middle region 102 or the distal region 128. The proximal region 104 is depicted extending from upstream boundary of the ureteral vesicle junction 120 to the inside the urinary bladder 124. The thinner wall of the proximal region 104 results from a greater inner diameter than the inner diameter present in the middle region 102. As a result, the wall in the proximal region 104 of the stent is thinner and is soft, floppy, and pliable compared to the middle region 102. The soft, floppy, and pliable characteristics of the proximal region 104 of the stent 100 substantially reduce the irritation of the ureteral vesical junction 120. A thin wall at the proximal region may alternatively be formed by a lesser outer diameter at the proximal region 104 than at the middle 102 or distal region 128. Alternatively, a combination of a lesser outer diameter and a greater inner diameter at the proximal region 104 than at the middle 102 or distal region 128 will also form a thin wall at the proximal region 104. FIG. 1B details the boundaries of the proximal region 104, middle region 102, and distal region 128. The elongated segment 101 is also shown.

FIGS. 2A–C, depict cross sections of various embodiments of the transition zone at the proximal region of the ureteral stent 100. In FIG. 2A, the transition zone 112 has no longitudinal length and forms a step that serves as a landing for a pusher. The transition zone 112 can also be a length greater than zero and still function as a landing. The transition zone 112 may also be a short region with a steep gradient in inner diameter (FIG. 2B). Alternatively, the transition zone 112 may extend into the proximal region 104 with a low rate increase in inner diameter (FIG. 2C); the rate of increase of the inner diameter may be linear as in FIG. 2B or non-linear following a curve as in FIG. 2C for example. The transition zone 112 may extend entirely along the proximal region 104. Optionally, the stent 100 may also include an embedded extraction thread 126 in the wall of the proximal region 104. An extraction thread 127 may also extend beyond the end of the proximal region 104. The extraction thread 127 may function as a structure suited for grasping during the removal of the stent 100 from the body.

Figure 3:
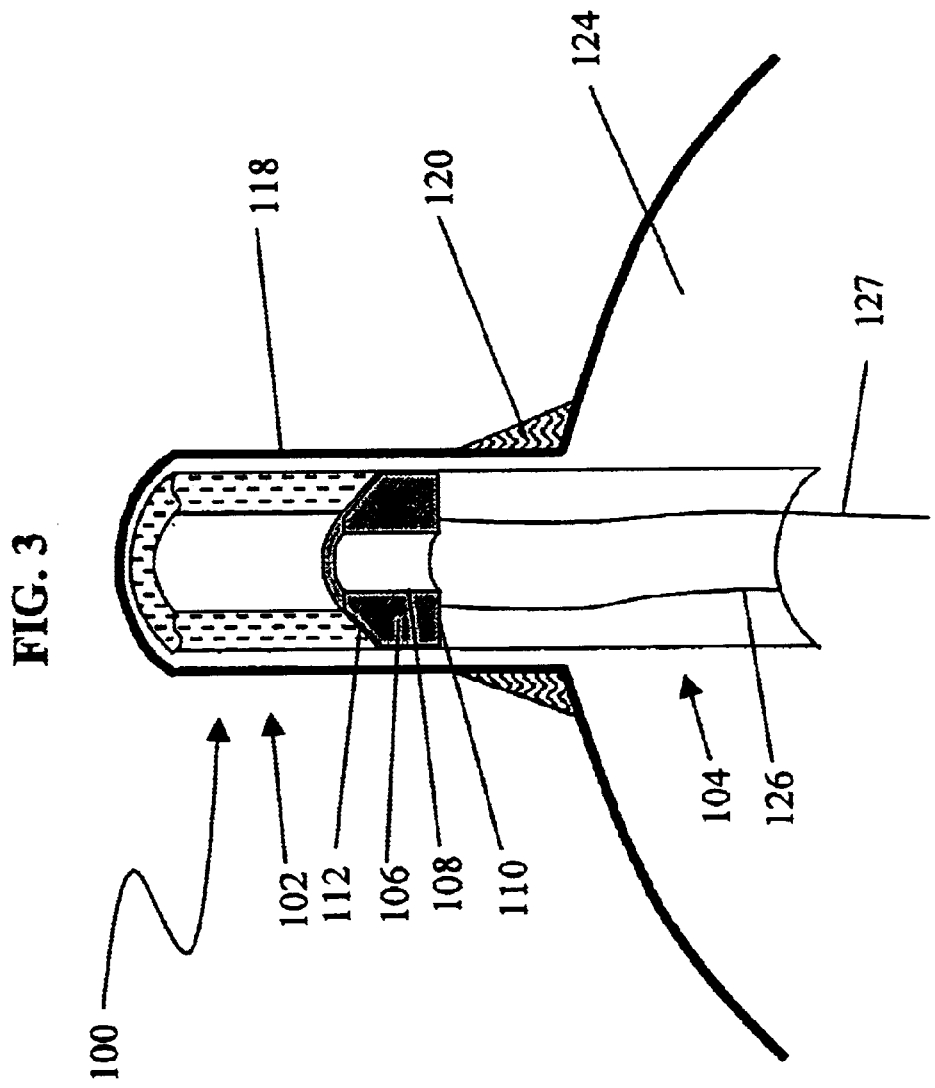
FIG. 3 depicts another embodiment of a proximal region of a medical device of the invention in longitudinal cross-section positioned in the ureter and urinary bladder.

Referring to FIG. 3, which depicts a cross-sectional view of the proximal region and a middle region of a stent of the invention. The stent 100 may further include a second segment 106 disposed near the transition zone 112. The inner wall 108 of the second segment 106 defines a lumen which is coaxial with the lumen of the stent 100. The second segment 106 is fixed in position in the inner of the stent 100. The second segment 106 may be fixed in position by an interference fit with, or by gluing or bonding, onto the inner wall of the stent, for example. The proximal end 110 of the second segment 106 serves as a landing for a pusher used to insert the stent 100 into the patient. The stent 100 may also include at least one extraction thread 126 embedded either in the wall of the proximal region 104, or at least partly in the transition zone 112 or middle region 102. The extraction thread 126 serves to reinforce the wall of the stent in the proximal region 104 by providing an embedded structural support of greater strength than the thin wall of the proximal region 104 provides. The purpose of the extraction thread is to prevent the thin wall of the proximal region 104 from tearing during the grasping of the proximal region 104 for the purpose of removing the stent. It also may be used to grasp onto and remove the stent 100 from the patient. The extraction thread 126 should be of sufficient tensile strength to serve as the handle by which the stent 100 is grabbed and removed. An extraction thread 127 may extend beyond the end of the proximal region 104. The extraction thread 127 may additionally serve as a graspable structure during the removal of the stent 100 from the ureter 118.

Figure 4:
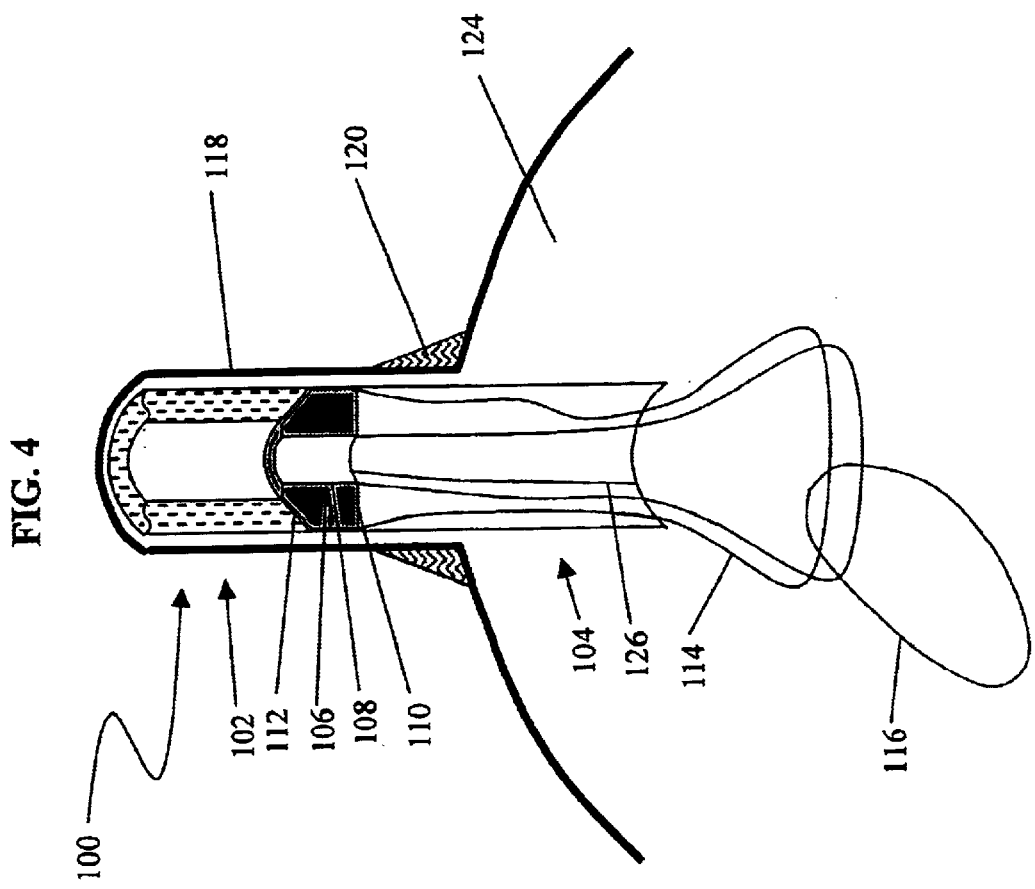
FIG. 4 depicts yet another embodiment of a proximal region of a medical device of the invention in longitudinal cross-section positioned in the ureter and urinary bladder.

Referring to FIG. 4, which shows the proximal region of a stent according to the invention the ureteral stent 100 may further include at least one member 114 that is connected to the second segment 106. A member 114 may comprise a thread, fiber, or filament. In this embodiment, both ends of each member 114 are connected to the proximal end 110 of second segment 106 such that the members form a loop. Alternatively, one or both ends of the members may be secured in the inner wall of the stent 100 or between the inner wall of the stent 100 and the exterior wall of the second segment 106. Members 114 may assist in the drainage of urine through the proximal region of the ureteral stent 100 by creating interstitial spaces between the members 114 themselves, the surrounding tissue, or stent wall 104 through which urine may pass. The member 114 may form a loop extending beyond the proximal end of the stent. The stent 100 may further include an extraction loop 116 that loops around at least one looped member 114 and is used to remove the stent 100 from the patient. The extraction loop 116 should also be of sufficient tensile strength and length to serve as the handle by which the stent 100 is grabbed and removed.

Referring to FIG. 5, which shows a cross sectional view of the proximal region of a stent according to the invention, the ureteral stent 100 may also further include at least one member 114 that is connected to the inner wall of the middle region 102. Alternatively, at least one member 114 may connect to the distal region 128 (not shown). The attachment of the member 114 may require that the member pass through the lumen of the middle region 102 and/or distal region 128 of the stent 100. The member 114 or members may assist in maintaining interstitial spaces within the lumen and maintain drainage should the stent 100 be compressed by peristaltic motion, for example. Attachment of the members 114 to the middle 102 or distal region of the stent 100 prevents the direct interference of the members 114 with the step 112 that serves as the landing for the pusher during insertion of the stent. The stent 100 may further include an extraction loop 116 that loops around the member 114.

Referring to FIG. 6, which shows a cross-sectional view of the proximal region of a stent according to the invention, the stent 100 includes a member 114 that is attached to the transition zone 112. The transition zone 112 is depicted having essentially no longitudinal length, thus forming a step in the inner diameter between the proximal region 104 and the middle region 102. The position of attachment of the member 114 to the landing should be configured such that, when inserting for positioning the stent in the ureter using a pusher, the pusher does not damage the member by compressing or bending the member 114 at its attachment site on the landing. Alternatively, the member may extend from the outside wall of the proximal region 104 or transition zone 112.

With cross-sectional views of the proximal region 104 of the stent, FIGS. 7A–H depict four examples of the many configurations that the wall of the proximal region 104 can fold into while the stent 100 is positioned in the body with (FIGS. 7E–H) and without (FIGS. 7A–D) members 114. FIGS. 7E–H illustrate how the members 114 assist in forming interstitial spaces 136 when the stent wall 104 becomes compressed. With members 114 (FIGS. 7E–H), the lumen is less susceptible to being compressed and collapsed to a point that hinders or blocks the flow of urine.

The stent of the invention may be used to treat a blockage of fluid flow between body cavities, for example from a kidney to the urinary bladder. The treatment of urine blockage within the kidney or ureter may be provided by inserting a ureteral stent according to the invention over a guide wire with a pusher through the urethra and urinary bladder to the final position in the ureter. The guide wire or a cannula may be used to temporarily straighten the retention structure in the distal region. The distal region is constructed from material that reforms its structure after having its shape distorted. This property of the material comprising the distal region allows for the retention structure at the distal region to be straightened during insertion of the stent into the body and still allowing the retention structure to reform into its original shape. The stent can also be inserted into position by use of an endoscope, ureteroscope, and a cytoscope, for example. Once the stent is located in the ureter it must be positioned so that the distal region is properly seated in the renal pelvis and the proximal end is located in the urinary bladder. Proper placement of the stent should also position the proximal thin-wall region over the ureteral vesical junction thus relieving irritation to this region and increasing patient comfort.

FIGS. 8A–F depict various embodiments of the proximal region of a stent according to the invention and the distal region of a pusher 132 contacting either the landing of the stent located at the transition zone 112 (FIGS. 8A–D) or the proximal end 110 of the second segment 106 (FIGS. 8E–F) as occurs during installation of the stent 100. The pusher 132 abuts and applies a force against the landing on the stent 100 to push the stent into the body of the patient during the installation of the stent 100. The distal end of the pusher 132 is adapted to the structure of the landing so that the force applied to the pusher 132 can be effectively transferred to the stent 100 so that installation can occur. In some instance the distal end 134 of the pusher may also extend slightly within the narrower lumen of the stent beyond the transition zone (FIGS. 8B and C) or the lumen of the second segment (FIG. 8F).

A guidewire 136 (FIGS. 8A and E) may function to assist in the installation of the stent. The guidewire 136 is inserted into the body, travelling through the urinary bladder and ureter until reaching the renal pelvis. Once the guidewire 136 is in the body, the stent 100 (FIGS. 8A and E) is inserted into the body by inserting the proximal end of the guidewire 136 into the lumen of the distal end of the stent 100 and by moving the stent 100 along the length of the guidewire 136, by the use of a pusher 132 (FIGS. 8A and E). The pusher 132 includes a lumen that is configured to accept a guidewire 136.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of embodiments of the invention is not intended to be limiting.

What is claimed is:

1. A medical device for assisting the drainage of fluid from a body cavity, comprising:
    an elongated segment extending from a distal region through a transition zone to a proximal region, said segment having a substantially constant outer diameter and an inner wall defining a lumen having an inner diameter in the proximal region that is greater than the inner diameter in the distal region, the proximal region comprising a pliable wall and a plurality of members, such that upon compression the members prevent hindrance or blockage of the drainage of the fluid.

2. The medical device of claim 1, wherein said device comprises a stent.

3. The medical device of claim 1, wherein said device comprises a ureteral stent.

4. The medical device of claim 1, wherein said transition zone comprises a step in the inner diameter between said proximal and distal regions.

5. The medical device of claim 1, wherein said transition zone comprises varying inner diameters between said proximal and distal regions.

6. The medical device of claim 1, further comprising at least one member extending through at least some of said lumen to said proximal region.

7. The medical device of claim 6, wherein said member comprises a flexible material.

8. The medical device of claim 6, wherein said member comprises a thread.

9. The medical device of claim 6, wherein said member is secured to the inner wall.

10. The medical device of claim 6, wherein said member comprises a substantially noncompressible material.

11. The medical device of claim 6, wherein said member includes a loop.

12. The medical device of claim 1, wherein said elongated segment further comprises a retention structure in the distal region.

13. The medical device of claim 1, wherein said elongated segment further comprises a kink resistant retention structure in the distal region.

14. The medical device of claim 1, wherein said elongated segment further comprises a coil in the distal region.

15. The medical device of claim 1, wherein said proximal region is flexible.

16. A medical device for assisting the drainage of fluid from a body cavity, comprising: an elongated segment extending from a distal region through a transition zone to a proximal region, said segment having a substantially constant outer diameter and an inner wall defining a lumen having an inner diameter in the proximal region that is greater than the inner diameter in the distal region; and a second segment comprising an exterior wall contacting at least a portion of the inner wall of said elongated segment, and further comprising an inner wall defining a lumen coaxial with said lumen of said elongated segment.

17. The medical device of claim 16, wherein said second segment further comprises a surface for contacting a pusher during implantation of said medical device in said body cavity.

18. The medical device of claim 16, wherein said transition zone comprises varying inner diameters between said proximal and distal regions.

19. The medical device of claim 16, wherein said exterior wall of said second segment provides an interference fit with said inner wall of said elongated segment.

20. The medical device of claim 16, wherein said device comprises a stent.

21. The medical device of claim 16, wherein said device comprises a ureteral stent.

22. The medical device of claim 16, further comprising at least one member extending from said inner tubular wall of said elongated segment.

23. The medical device of claim 16, further comprising at least one member extending from said second segment.

24. The medical device of claim 16, wherein said member comprises a flexible material.

25. The medical device of claim 16, wherein said member comprises a thread.

26. The medical device of claim 16, wherein said member comprises a substantially noncompressible material.

27. The medical device of claim 16, wherein said member includes a loop.

28. The medical device of claim 16, wherein said elongated segment further comprises a retention structure in the distal region.

29. The medical device of claim 16, wherein said elongated segment further comprises a kink resistant retention structure in the distal region.

30. The medical device of claim 29, wherein said retention structure includes a coil.

31. The medical device of claim 16, wherein said proximal region is pliable.

32. A medical device for assisting the drainage of fluid from a body cavity, said device comprising an elongated segment having an annular wall defining a lumen, said lumen extending from a distal opening to a proximal opening, a proximal region of the elongated segment comprising a pliable section of the annular wall and a plurality of members, such that upon compression the members prevent hindrance or blockage of the drainage of the fluid; said annular wall having a thickness near said distal opening greater than near said proximal opening, wherein said elongated segment is kink resistant near said distal opening arid pliable near said proximal opening.

33. The medical device of claim 32, wherein said device comprises a stent.

34. The medical device of claim 32, wherein said device comprises a ureteral stent.

35. The medical device of claim 32, further comprising at least one member extending from and attached to said elongated segment.

36. The medical device of claim 32, wherein said member comprises a thread.

37. A method for treatment of blockage of urine flow from a kidney to a urinary bladder, the method comprising:

a) providing a medical device for assisting the drainage of fluid from a body cavity, comprising an elongated segment extending from a distal region through a transition zone to a proximal region, said segment having a substantially constant outer diameter and an inner wall defining a lumen having an inner diameter in the proximal region that is greater than the inner diameter in the distal region, the proximal region comprising a pliable wall and a plurality of members, such that upon compression the members prevent hindrance or blockage of the drainage of the fluid; and b) inserting said device in a ureter.

38. A method of claim 37, further positioning said distal region of said medical device near a renal pelvis; and positioning said proximal region of said medical device in a urinary bladder.

39. A method of claim 37, further comprising a pusher contacting a surface of the stent in the transition zone.

40. A method for treatment of blockage of urine flow from a kidney to a urinary bladder, the method comprising:

a) providing a medical device for assisting the drainage of fluid from a body cavity, comprising an elongated segment extending from a distal region through a transition zone to a proximal region, said segment having a substantially constant outer diameter and an inner wall defining a lumen having an inner diameter in the proximal region that is greater than the inner diameter in the distal region; and a second segment comprising an exterior wall contacting at least a portion of the inner wall in the distal region of said elongated segment, and further comprising an inner wall defining a lumen coaxial with said lumen of said elongated segment; and b) inserting said device into a ureter.

41. A method of claim 40, further positioning said distal region of said medical device near a renal pelvis; and positioning said proximal region of said medical device in a urinary bladder.

42. A method of claim 40, further comprising a pusher contacting a surface on said second segment disposed within the lumen of the stent near the transition zone.

43. A method for treatment of blockage of urine flow from a kidney to a urinary bladder, the method comprising:

a) providing a medical device for assisting the drainage of fluid from a body cavity, said device comprising an elongated segment having an annular wall defining said lumen, said lumen extending from a distal opening to a proximal opening, a proximal region of the elongated segment comprising a pliable wall and a plurality of members, such that upon compression the members prevent hindrance or blockage of the drainage of the fluid; said annular wall having a thickness near said distal opening greater than near said proximal opening, wherein said elongated segment is kink resistant near said distal opening and pliable neat said proximal opening; and b) inserting said device into a ureter.

44. A method of claim 43, further positioning said distal region of said medical device near a renal pelvis; and positioning said proximal region of said medical device in a urinary bladder.

45. A method of claim 43, further comprising a pusher contacting a surface of the stent in the transition zone.

* * * * *